United States Patent
Tom et al.

(10) Patent No.: US 7,427,346 B2
(45) Date of Patent: Sep. 23, 2008

(54) ELECTROCHEMICAL DRIVE CIRCUITRY AND METHOD

(75) Inventors: Glenn M. Tom, New Milford, CT (US); Steven Lurcott, Sherman, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 435 days.

(21) Appl. No.: 10/838,390

(22) Filed: May 4, 2004

(65) Prior Publication Data

US 2005/0247576 A1   Nov. 10, 2005

(51) Int. Cl.
*G01N 27/42* (2006.01)
(52) U.S. Cl. .................. 205/775; 204/406; 204/434
(58) Field of Classification Search ............... 204/406, 204/434
See application file for complete search history.

(56) References Cited

U.S. PATENT DOCUMENTS

| | | | |
|---|---|---|---|
| 2,707,166 A | 4/1955 | Brown et al. | |
| 2,707,167 A | 4/1955 | Hoover et al. | |
| 2,830,014 A | 4/1958 | Gundel et al. | |
| 2,884,366 A | 4/1959 | Anderson et al. | |
| 2,898,282 A | 8/1959 | Flook, Jr. et al. | |
| 3,101,305 A | 8/1963 | Roth et al. | |
| 3,276,979 A | 10/1966 | Strauss et al. | |
| 3,288,690 A | 11/1966 | Creutz et al. | |
| 3,655,534 A | 4/1972 | Kampe | |
| 3,725,220 A | 4/1973 | Kessler | |
| 3,798,138 A | 3/1974 | Ostrow et al. | |
| 3,883,414 A | 5/1975 | Fujinaga et al. | |
| 3,910,830 A | 10/1975 | Mayse | |
| 3,950,234 A | 4/1976 | Faulkner et al. | |
| 3,972,789 A | 8/1976 | Eppensteiner et al. | |
| 3,996,124 A | 12/1976 | Eaton et al. | |
| 4,038,161 A | 7/1977 | Eckles et al. | |
| 4,071,429 A | 1/1978 | Wagenknecht et al. | |
| 4,119,532 A | 10/1978 | Park | |

(Continued)

FOREIGN PATENT DOCUMENTS

DE   19911447 A1   12/2000

(Continued)

OTHER PUBLICATIONS

Alexander Milchev, "A Galvanostatic Study of Electrochemical Nucleation", J. Electroanal. Chem., 333 (1992), 93-102.

(Continued)

*Primary Examiner*—Kaj K Olsen
(74) *Attorney, Agent, or Firm*—Steven J. Hultquist; Intellectual Property/ Technology Law; Margaret Chappuis

(57) ABSTRACT

An electrochemical drive circuitry and method, such as may be employed in electroplating bath chemical monitoring. A microcontroller can be utilized to selectively apply galvanostatic or potentiostatic conditions on the electrochemical cell, for measurement of response of the electrochemical cell to such conditions, with the microcontroller arranged to generate an offset potential to control potential across the electrochemical cell within a range of potential accommodated by a unipolar power supply, and/or a CMOS analog switch can be employed in combination with individual digital-to-analog converters for each of the current-controlled and potential-controlled conditions, to provide high-speed, dual mode operating capability.

19 Claims, 2 Drawing Sheets

U.S. PATENT DOCUMENTS

| | | | |
|---|---|---|---|
| 4,132,605 A | | 1/1979 | Tench et al. |
| 4,260,950 A | | 4/1981 | Hadden et al. |
| 4,305,039 A | * | 12/1981 | Steuernagel et al. ........ 324/425 |
| 4,317,002 A | | 2/1982 | Spicer |
| 4,388,165 A | | 6/1983 | Koshiishi et al. |
| 4,496,454 A | | 1/1985 | Berger |
| 4,498,039 A | * | 2/1985 | Galwey et al. .............. 323/234 |
| 4,529,495 A | | 7/1985 | Marsoner |
| 4,568,445 A | | 2/1986 | Cates et al. |
| 4,589,958 A | | 5/1986 | Alexander et al. |
| 4,595,462 A | | 6/1986 | Vangaever et al. |
| 4,707,378 A | | 11/1987 | McBride et al. |
| 4,772,375 A | | 9/1988 | Wullschleger et al. |
| 4,812,210 A | | 3/1989 | Bonivert et al. |
| 4,849,330 A | | 7/1989 | Humphries et al. |
| 4,917,774 A | | 4/1990 | Fisher |
| 4,917,777 A | | 4/1990 | Fisher |
| 5,017,860 A | * | 5/1991 | Germer et al. .............. 324/142 |
| 5,074,157 A | | 12/1991 | Marsoner et al. |
| 5,131,999 A | | 7/1992 | Gunasingham |
| 5,162,077 A | | 11/1992 | Bryan et al. |
| 5,192,403 A | | 3/1993 | Chang et al. |
| 5,223,118 A | | 6/1993 | Sonnenberg et al. |
| 5,268,087 A | | 12/1993 | Lu |
| 5,288,387 A | | 2/1994 | Ito et al. |
| 5,296,123 A | | 3/1994 | Reddy et al. |
| 5,316,649 A | | 5/1994 | Kronberg |
| 5,320,721 A | | 6/1994 | Ludwig et al. |
| 5,325,038 A | * | 6/1994 | Banzai et al. ............... 320/135 |
| 5,352,350 A | | 10/1994 | Andricacos et al. |
| 5,404,018 A | | 4/1995 | Yasuda et al. |
| 5,447,802 A | | 9/1995 | Tobiyama et al. |
| 5,462,645 A | | 10/1995 | Albery et al. |
| 5,612,698 A | * | 3/1997 | Reay .......................... 341/167 |
| 5,635,043 A | | 6/1997 | Tur'yan et al. |
| 6,022,470 A | | 2/2000 | Yarnitzky |
| 6,210,640 B1 | | 4/2001 | Ruth et al. |
| 6,231,743 B1 | | 5/2001 | Etherington |
| 6,254,760 B1 | | 7/2001 | Shen et al. |
| 6,270,651 B1 | | 8/2001 | Essalik et al. |
| 6,280,602 B1 | | 8/2001 | Robinson |
| 6,288,783 B1 | | 9/2001 | Auad |
| 6,365,033 B1 | | 4/2002 | Graham et al. |
| 6,366,794 B1 | * | 4/2002 | Moussy et al. .............. 600/345 |
| 6,395,152 B1 | * | 5/2002 | Wang .................... 204/224 M |
| 6,409,903 B1 | | 6/2002 | Chung et al. |
| 6,458,262 B1 | | 10/2002 | Reid |
| 6,459,011 B1 | | 10/2002 | Tarr et al. |
| 6,478,950 B1 | | 11/2002 | Peat et al. |
| 6,495,011 B2 | | 12/2002 | Robertson |
| 6,558,519 B1 | | 5/2003 | Dodgson et al. |
| 6,569,307 B2 | | 5/2003 | Blachier et al. |
| 6,572,753 B2 | | 6/2003 | Chalyt et al. |
| 6,592,737 B1 | * | 7/2003 | Robertson .................... 205/81 |
| 6,645,364 B2 | | 11/2003 | Calvert et al. |
| 6,673,226 B1 | | 1/2004 | Kogan et al. |
| 6,709,568 B2 | | 3/2004 | Han et al. |
| 6,758,955 B2 | | 7/2004 | Robertson |
| 6,758,960 B1 | | 7/2004 | Robertson |
| 6,808,611 B2 | | 10/2004 | Sun et al. |
| 6,827,839 B2 | | 12/2004 | Sonnenberg et al. |
| 6,974,531 B2 | | 12/2005 | Andricacos et al. |
| 7,022,215 B2 | | 4/2006 | Schomburg |
| 6,984,299 B2 | | 6/2006 | Han et al. |
| 7,094,323 B2 | | 8/2006 | King et al. |
| 2002/0070708 A1 | * | 6/2002 | Wu ............................. 320/134 |
| 2003/0080000 A1 | | 5/2003 | Robinson |
| 2004/0040842 A1 | | 3/2004 | King et al. |
| 2004/0055888 A1 | | 3/2004 | Wikiel et al. |
| 2004/0065561 A1 | | 4/2004 | Chalyt et al. |
| 2005/0016847 A1 | * | 1/2005 | Buehler ....................... 204/412 |
| 2005/0067304 A1 | | 3/2005 | King et al. |
| 2005/0109624 A1 | | 5/2005 | King et al. |
| 2005/0224370 A1 | | 10/2005 | Liu et al. |
| 2005/0241948 A1 | | 11/2005 | Han et al. |
| 2006/0102475 A1 | | 5/2006 | Han et al. |
| 2006/0266648 A1 | | 11/2006 | King et al. |

FOREIGN PATENT DOCUMENTS

| | | |
|---|---|---|
| EP | 0 302 009 A1 | 7/1988 |
| JP | 2001-073183 A | 3/2001 |
| WO | WO 01/29548 A1 | 4/2001 |

OTHER PUBLICATIONS

"Aldrich Handbook of Fine Chemicals and Laboratory Equipment", 2003-2004, pp. 500, 501 and 1634, Publisher: Aldrich Chemical Co., Published in: Milwaukee, WI.

Bard, Allen J., et al., Electrochemical Methods: Fundamentals and Applications, 2nd Edition, 2001, pp. 15-16, Publisher: John Wiley & Sons, Inc., Published in: New York.

Freitag, Walter O., et al., Determination of the individual additive components in acid copper plating baths, Plat. Surf. Fin., Oct. 1983, pp. 55-60, vol. 70, No. 10.

Healy, John P., et al., The chemistry of the additives in an acid copper electroplating bath: Part II. The instability 4,5-dithiaoctane-1, . . . , J. Electoanal. Chem., Oct. 1992, pp. 167-177, vol. 338, No. 1-2.

Healy, John P., et al., The chemistry of the additives in an acid copper electroplating bath: Part III. The mechanism of brightening by 4,5-. . . , J. Electroanal. Chem., Oct. 1992, pp. 179-187, vol. 338, No. 1-2.

Huiliang, Huang, et al., Flow potentiometric and constant-current stripping analysis for mercury(II) with gold, platinum and carbon fibre . . . , Analytica Chimica Acta, 1987, pp. 1-9, vol. 201.

Kim, Jae Jeong, et al., Catalytic behavior of 3-mercapto-1-propane sulfonic acid on Cu electrodeposition and its effect on Cu film properties . . . , J. Electronanal. Chem., Jan. 30, 2003, pp. 61-66, vol. 542, No. 1.

Liu, Yonghui, Testing Technology of Electrochemistry, (English relevance attached), 1987, p. 159, Published in: Beijing.

Metrohm, Product description of 731 Relay Box, Downloaded May 11, 2005 from http://www.metrohm.com/products/05/acc/731/731.html, May 11, 2005.

Metrohm, Product description of 772 Pump Unit, Downloaded May 11, 2005 from http://www.metrohm.com/products/05/acc/772/772.html, May 11, 2005.

Metrohm, Product description of MVA-3 voltammetry system, Downloaded May 11, 2005 from http://www.metrohm.com/products/06/mva/mva03/mva03.html, May 6, 2004.

Metrohm, Product description of Titrando Dosino, http://www.metrohm.com/titrando/products/units/800/800.html, 2003.

Metrohm, Product description of Titrando PC Control, Downloaded May 11, 2005 from http://www.metrohm.com/titrando/products/control/pc/pc.html, 2004.

Milchev, Alexander, et al., A galvanostatic study of electrochemical nucleation, J. Electrocanal. Chem., Jul. 25, 1992, pp. 93-102, vol. 333, No. 1-2.

Oldham, Keith B., et al., Fundamentals of Electrochemical Science, 1994, pp. 328-332, Publisher: Academic Press, Inc., Published in: San Diego.

Tench, Dennis, et al., Cyclic pulse voltammetric stripping analysis of acid copper plating baths, J. Electrochem. Soc., Apr. 1985, pp. 831-834, vol. 132, No. 4.

Vereecken, P.M., et al., The chemistry of additives in damascene copper plating, IBM J. Res. Dev., Jan. 2005, pp. 3-18, vol. 49, No. 1.

Wojciechowski, Marek, et al., Square-wave anodic stripping voltammetry of lead and cadmium at cylindrical graphite fiber microelectrodes with . . . , Analytica Chimica Acta, 1991, pp. 433-445, vol. 249, No. 2.

Wikipedia, Universal Serial Bus—Wikipedia, Downloaded May 11, 2005 from hhtp://en.wikipedia.org/wiki/USB, May 11, 2005.

* cited by examiner

US 7,427,346 B2

ELECTROCHEMICAL DRIVE CIRCUITRY AND METHOD

BACKGROUND OF THE INVENTION

1. Field of the Invention

The present invention relates generally to an electrochemical drive circuitry and method, such as may be employed in electroplating bath chemical monitoring.

2. Description of the Related Art

In the practice of copper interconnect technology in semiconductor manufacturing, electrolytic deposition is widely employed for forming interconnect structures on microelectronic substrates. The Damascene process, for example, uses physical vapor deposition to deposit a seed layer on a barrier layer, followed by electrochemical deposition (ECD) of copper. Copper ECD on the seed layer produces void-free fills in high aspect ratio features and is a process methodology of choice for metallization of the semiconductor substrate.

ECD of copper as conventionally carried out depends on use of organic additives in the plating solution of the bath in which the deposition is carried out. The bath also contains inorganic additives, and the ECD process is sensitive to concentration of both organic and inorganic components, since these components can vary considerably as they are consumed during the life of the bath. Only by real-time monitoring and replenishment of all major bath components can the semiconductor manufacturing process be assured of optimal process efficiency and yield.

The inorganics in the copper ECD bath include copper, sulfuric acid and chloride species, which may be measured by potentiometric analysis. Organic additives are added to the ECD bath to control the uniformity of the film thickness across the wafer surface, and include suppressor, accelerator and leveler species. The concentration of organic additives may be measured by cyclic voltammetry or impedence methods, or by pulsed cyclic galvanostatic analysis (PCGA), which mimics the plating conditions occurring on the wafer surface. PCGA is frequently used, and employs a double pulse for nucleation and subsequent film growth on the electrode, in performing abbreviated electrolysis sequences and using analytical sensors to measure the ease of metal deposition. Through chemical masking and monitoring of the plating potential, additive concentrations are readily determined.

A chemical analysis system that is advantageously employed for monitoring of copper ECD processes, utilizing potentiometric analysis for monitoring of inorganic components of the ECD bath, and PCGA analysis for monitoring of organic components, is commercially available from ATMI, Inc. (Danbury, Conn., USA) under the trademark CuChem. Such system utilizes a working electrode, typically formed of platinum, on which copper is cyclically plated, in a process sequence of cleaning, equilibration, plating and stripping.

In the operation of the CuChem™ system, it has been observed that in some instances the stripping operation tends to drive the platinum electrode to an excessively anodic condition. This anodic condition in turn results in changes in the state of the working electrode and loss of performance over time. Although such excessively anodic condition can be ameliorated to some extent by reducing the duration of the working electrode stripping step, and/or reducing current density in the working electrode, there is a need for a monitoring system that is free of such excessive anodicity in the working electrode.

Considering the electrochemical cell of the ECD monitoring system in further detail, with respect to potentiostatic measurements, in which a controlled voltage is imposed on the cell and resulting current is measured, and galvanostatic measurements, in which a controlled current is induced on the cell and the resulting voltage is measured, various configurations of analog circuitry have been successfully employed in monitoring systems.

In the application of such analog circuitry, measurement of both potentiostatic currents and galvanostatic voltages requires analog circuits including analog or mechanical switches, numerous operational amplifiers and even more numerous resistors. Each of such components of the analog circuit is both an error source and a noise source. The error/noise issues associated with such analog circuit componentry become even more significant in the nanoamp ($10^{-9}$ amp) signal region that is desired for next generation ECD monitoring systems. Additionally, the desired use of a unipolar power supply in such nanoamp regime requires even more complexity of the analog circuitry, which also further increases the error and noise levels in the electrochemical process monitoring circuitry.

It therefore is desirable to provide ECD monitoring circuitry that affords a solution to such issues of circuit complexity, noise, accuracy, dual mode (potentiostatic mode and galvanostatic mode) operation, and unipolar power supply usage.

SUMMARY OF THE INVENTION

The present invention relates generally to an electrochemical drive circuitry and method, such as may be employed in electroplating bath chemical monitoring.

In one aspect, the invention relates to circuitry for monitoring an electrochemical process including an electrochemical cell, in which the circuitry includes a microcontroller programmably arranged in a feedback loop with the electrochemical cell, for switching between galvanostatic and potentiostatic modes of operation of the electrochemical cell.

In another aspect, the invention relates to an electrochemical process monitoring system, comprising:

an electrochemical cell including a working electrode, and arranged for monitoring an electrochemical deposition process by sequential steps including plating on the working electrode, under current controlled conditions, and stripping of plated material from the working electrode, cyclic voltammetry, equilibration and nucleation of plating material on the working electrode, under potential controlled conditions;

a drive circuit coupled to the electrochemical cell and arranged to apply current controlled conditions on the electrochemical cell during said plating step, and to apply potential controlled conditions on the electrochemical cell during the stripping, cyclic voltammetry, equilibration and nucleation steps;

wherein the drive circuit comprises a CMOS analog switch including a first set of switch positions connectable to one another to apply the current controlled conditions on the electrochemical cell, and a second set of switch positions connectable to one another to apply the potential controlled conditions on the electrochemical cell.

A further aspect of the invention relates to a method of monitoring an electrochemical process in an electrochemical cell, wherein said method comprises use of an apparatus selected from the group consisting of (i) a circuitry as described in paragraph [0013] hereof, and (ii) a system as described in paragraphs [0014] thru [0017] hereof.

Yet another aspect of the invention relates to a method of monitoring an electrochemical process in an electrochemical cell, comprising use of a microcontroller to selectively apply galvanostatic or potentiostatic conditions on the electrochemical cell, for measurement of response of the electrochemical cell to such conditions, wherein the microcontroller is arranged to generate an offset potential to control potential across the electrochemical cell within a range of potential accommodated by a unipolar power supply.

A still further aspect of the invention relates to a method of monitoring an electrochemical process using an electrochemical cell including a working electrode, comprising:

plating on the working electrode, under current controlled conditions, and stripping of plated material from the working electrode, cyclic voltammetry, equilibration and nucleation of plating material on the working electrode, under potential controlled conditions;

providing drive circuitry for the electrochemical cell including a CMOS analog switch arranged for switching between the current controlled conditions and the potential controlled conditions, a first digital-to-analog converter arranged for operation under the current controlled conditions, and a second digital-to-analog converter arranged for operation under the potential controlled conditions;

setting a setpoint of each of the digital-to-analog converters before transition to such digital-to-analog converter from the other of the digital-to-analog converters, so that each of the digital-to-analog converters has a rise time upon switching that is less than 1 millisecond;

changing from one of the current controlled and potential controlled conditions to the other of the current controlled and potential controlled conditions by switching of the CMOS analog switch, with transition from one of the digital-to-analog converters to the other of the digital-to-analog converters incident to such switching.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
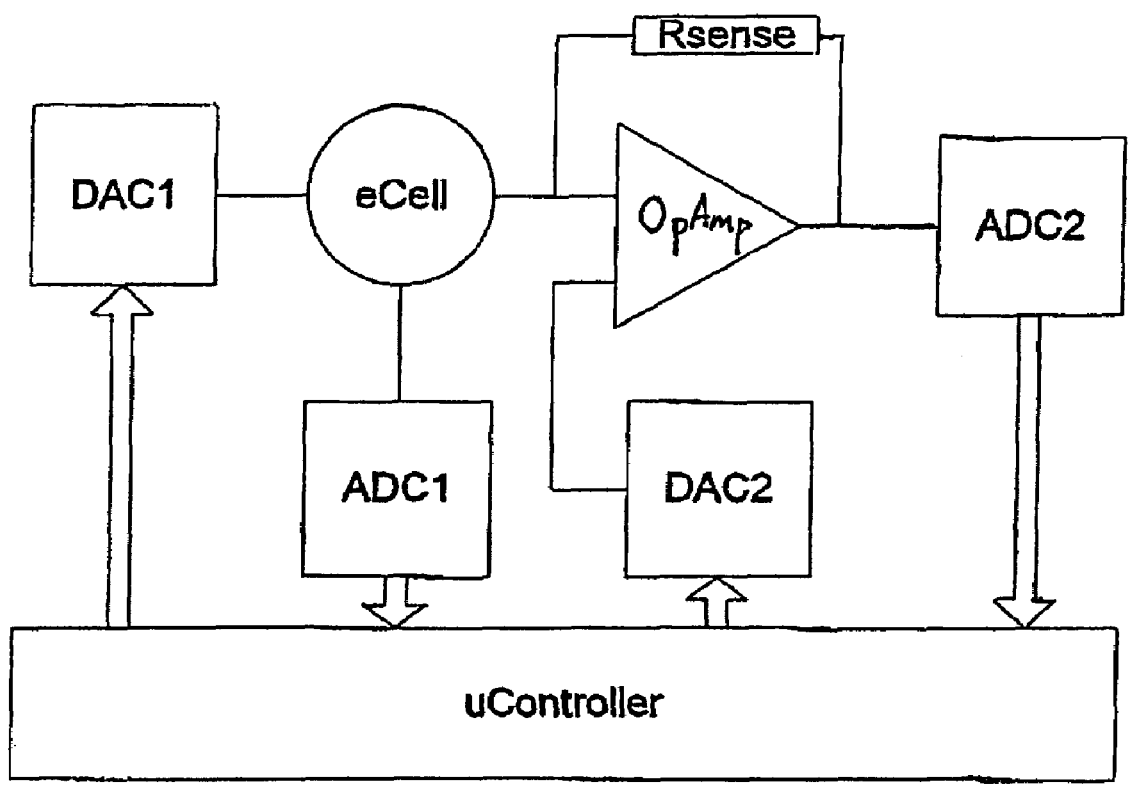
FIG. 1 is a schematic representation of an electrochemical system monitoring circuit according to one embodiment of the invention.

The disclosures of the following U.S. Patent Publication and U.S. Patents are incorporated herein by reference in their respective entireties for all purposes: U.S. Patent Publication No. US2003 0080000 A1 published May 1, 2003 in the name of Peter M. Robinson for "Interference Correction of Additives Concentration Measurements in Metal Electroplating Solutions;" U.S. Pat. No. 6,280,602 issued Aug. 28, 2001 to Peter M. Robinson for "Method and Apparatus for Determination of Additives in Metal Plating Baths;" U.S. Pat. No. 6,592,737 issued Jul. 15, 2003 to Peter M. Robinson for "Method and Apparatus for Determination of Additives in Metal Plating Baths;" and U.S. Pat. No. 6,709,568 issued Mar. 23, 2004 to Jianwen Han, et al. for "Method for Determining Concentrations of Additives in Acid Copper Electrochemical Deposition Baths."

In the circuitry discussed more fully hereinafter, the connections of components in the circuitry may be effected in a manner within the skill of the art, based on the disclosure herein, using signal transmission lines, couplings, interconnects, metallization and the like. The response of the electrochemical monitoring cell will variously include current and/or potential characteristics that can be outputted to elements such as ammeters or voltmeters, or to computational means, such as a central processing unit, microprocessor, programmable general purpose digital computer, or the like, for signal processing of the electrochemical cell output to produce useful data for monitoring and control of an electrochemical process of interest via the electrochemical monitoring cell.

The present invention provides a microcontroller-based circuitry that addresses the previously discussed issues of circuit complexity, noise, accuracy, dual mode (potentiostatic mode and galvanostatic mode) operation, and unipolar power supply usage in ECD process monitoring systems.

By arranging a microcontroller in a feedback loop, the associated monitoring system software is able to switch between galvanostatic and potentiostatic modes of operation with no analog switching. System measurements are made directly and the system is able to operate at a suitable potential permitting use of a unipolar power supply. An offset is injected that is consistent with the required operating potential range of the electrochemical monitoring circuitry. The microcontroller modulates the offset in such manner as to control the potential across the electrochemical cell within a range accommodated by the unipolar power supply.

The microcontroller may be programmably arranged for such operation by appropriate software/firmware, within the skill of the art, based on the disclosure herein.

For example, if the electrochemical monitoring system has a required range of operation of from −2 volts to +2 volts, the injection of an offset of 2.5 volts provides the monitoring system with a corresponding range of operation of −2.5 to +2.5 volts across the electrochemical cell. Since the microcontroller can modulate the offset, a range of operation of −5 volts to +5 volts across the cell is possible using only a unipolar 5 volt power supply. Setting the offset to 0 volts enables 0 volts to 5 volts operation, and setting the offset to 5 volts enables −5 volts to 0 volt operation.

FIG. 1 shows an electrochemical system monitoring circuit according to one embodiment of the invention, including a microcontroller ("uController") arranged to receive digital input signals from an analog-to-digital converter ("ADC1") linked to the electrochemical cell ("eCell"), and an analog-to-digital converter ("ADC2") linked to the output of the operational amplifier ("OpAmp").

The OpAmp has a current measurement scaling unit ("Rsense") coupled between its output and its inverting input, as shown, with the inverting input being linked to the eCell.

The uController is arranged for transmitting a digital output signal to a digital-to-analog converter ("DAC1") linked to the eCell, and for transmitting a digital output signal to a digital-to-analog converter ("DAC2") that is linked to the non-inverting input of the OpAmp.

In potentiostatic operation of the measurement circuit shown in FIG. 1, DAC2 sets the offset in response to a control signal from uController. The offset may be any suitable voltage value appropriate to the system. In one embodiment of the invention, such offset is 2.5 volts. The OpAmp is configured to amplify the current required to maintain the offset voltage, so that the OpAmp functions as a low impedance virtual ground.

The Rsense unit sets the scaling for the current measurement. ADC2 is used by uController to measure the current, and DAC1 is used to set the fixed voltage (relative to DAC2) for the desired measurement.

In the galvanostatic (controlled current) mode, uController monitors ADC2 for the actual current passing through eCell and modulates DAC1 accordingly. DAC2 is still utilized to set the offset, as described above. ADC1 is employed to monitor the voltage in eCell. Although not shown for ease of illustration, it may be advantageous in some instances where low signal levels are present to utilize a buffer between eCell and ADC1, depending on the input impedance of ADC1.

The microcontroller circuitry arrangement shown in FIG. 1 thus enables a unipolar power supply to be employed, which accommodates dual mode (potentiostatic and galvanostatic) operation without analog switching, and without a high complexity circuit that would otherwise entail significantly increased noise and significantly reduced accuracy, if conventional analog circuitry involving analog or mechanical switches were employed.

The invention further provides drive circuitry for an electrochemical analysis cell that is suited for conducting pulsed cyclic galvanostatic analysis of organic components in the plating bath, without the incidence of excessive anodicity of the working electrode during the stripping step, such as would otherwise progressively degrade the performance of the measuring system over time.

Figure 2:
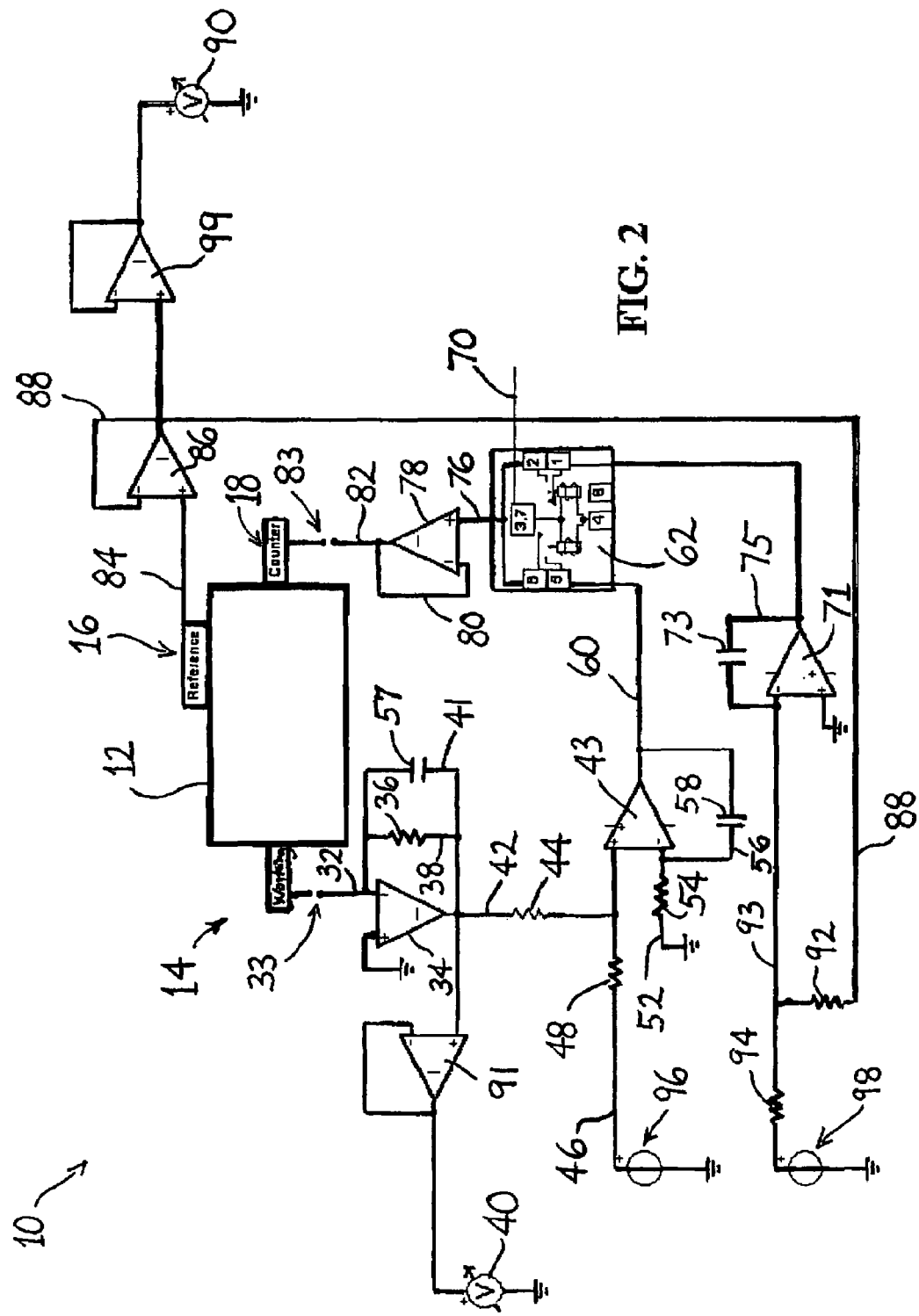
FIG. 2 is a schematic representation of the circuitry of a PCGA system including a drive circuit according to one embodiment of the invention.

FIG. 2 is a schematic representation of the circuitry 10 of a system including a drive circuit for an electrochemical analysis cell, according to another embodiment of the invention.

The system includes an electrochemical cell 12 featuring a working electrode 14, a reference electrode 16 and a counter electrode 18. The circuitry 10 of the system further includes relays 33 and 83 to provide open circuit capability so that the electrochemical cell 12 can be rendered electrically inactive when fluids in the cell are changed.

The circuitry in FIG. 2 functions to keep leakage currents from affecting the monitoring measurements of the system. The input bias currents of op-amp 34, op-amp 78 and op-amp 86 are on the order of 1 picoamp, so that negligible current is drawn by the op-amps, such as could otherwise perturb the system measurements. Additionally, the circuitry includes op am buffers 91 and 99 between the control circuitry and the data acquisition system, to ensure that no noise is injected by the data acquisition system back into the control loops of the circuitry. The op amps in the circuitry may be of any suitable type, such as TLC4501 single-channel self-calibrating operational amps, commercially available from Texas Instruments (Dallas, Tex., USA).

The circuitry of FIG. 2 accommodates the speed requirements of the PCGA process for continuous on-line real-time monitoring, using algorithms in which the time domain of interest is generally less than the first 10 seconds of operation, e.g., the first 2 to 5 seconds of operation. The transition between the steps must be of a clean character, and is accommodated by the circuitry arrangement including the CMOS analog switch 62 and dual digital-to-analog converters 96 and 98 of the system. For such purpose, the circuitry shown in FIG. 2 may be coupled with a central processing unit (CPU), microprocessor, or other computational module, means or unit, for generating an output indicative of the concentrations of the plating bath components of interest, or the deviations of such concentrations from set point values, in a manner readily effected by those skilled in the art based on the disclosure herein.

The measurement carried out by PCGA in the system of FIG. 2 includes current control during the plating operation, and potential control during the stripping, cyclic voltammetry, equilibration and nucleation phases. This is accommodated by the CMOS analog switch 62. When potential control is required, positions "1" and "2" are connected by the relay, and when galvanostatic control is required, positions "5" and "6" are connected. The switch is free of "bounce" effects associated with operation of mechanical switches, and thereby achieves a clean edge (demarcation) between the two states of potential control and galvanostatic control. The CMOS analog switch affords fast switching, with transition times that may for example be on the order of 150 nanoseconds.

Two digital-to-analog converters 96 and 98 are employed to rapidly bring the system to the correct current or potential condition, respectively. The rise time of digital-to-analog converters is on the order of 2 milliseconds, which is too slow for slewing from rail to proper setpoints. With individual digital-to-analog converters, individual setpoints can be set before the occurrence of the transition from the other (current control or potential control) state, so that the rise time is substantially faster, being generally <1 millisecond, and more preferably <<1 millisecond, e.g., 250 microseconds.

The circuitry 10 includes reference electrode line 84 to the positive input of op amp 86, whose negative input is connected by line 88, having resistor 92 (10 k-ohms) therein, to line 93 having resistor 94 (10 k-ohms) therein and linking the potential control digital-to-analog converter 98 with the inverting input of op amp 71 having capacitor 73 (1 microFarad) in line 75 associated therewith. The output of op amp 86 is connected to voltmeter 90, with buffer op amp 99 therebetween. The output of op amp 71 is coupled with position 1 of the CMOS analog switch 62.

The working electrode 14 of the electrochemical cell 12 is connected by line 32, having relay 33 therein, to the negative input of op amp 34, having resistor 36 (100 k-ohms) in loop 38, and capacitor 57 (82 picoFarads) in loop 41 associated therewith. The output of the op amp 34 is coupled to voltmeter 40, with buffer op am 91 therebetween. The output of the op amp 34 also is joined by line 42, having resistor 44 (100 k-ohms) therein, to line 46 having resistor 48 (100 k-ohms) therein and linking digital-to-analog converter 96 with the positive input of op amp 43. The negative input of op amp 43 is coupled with the output of such op amp by loop 56 containing capacitor 58 (150 picoFarads) therein. Loop 56 connects to the grounded inverting input line 52 of op amp 43, having resistor 54 (47 k-ohms) therein.

Output line 60 of op amp 43 is connected to position 5 of the CMOS analog switch 62. The CMOS analog switch 62 has associated therewith a line 70, interconnecting positions 3,7 of the CMOS analog switch 62 with a power supply (not shown) that in turn is coupled with positions 4 and 8 of the CMOS analog switch 62, for operation of the circuitry in the described manner.

Counter electrode 18 of the electrochemical cell 12 is coupled by line 82, having relay 83 therein, with the output of op amp 78 having loop 80 associated therewith. The positive input of op amp 78 is joined by line 76 to branches in the CMOS analog switch 62 connecting to positions 2 and 6 of the CMOS analog switch.

The circuitry shown in FIG. 2 is characterized by low leakage currents, clean transitions between current control plating operation and potential control during stripping, cyclic voltammetry, equilibration and nucleation steps, and fast transitions in consequence of the dual digital-to-analog converters and CMOS analog switch, to permit switching between current controlled and potential controlled modes of operation, in a highly effective manner. Such circuitry permits the stripping step to be efficiently carried out without excessive anodicity of the working electrode, with the result that the working electrode is maintained in a highly stable state with good performance even after extended periods of operation.

Although the invention has been variously described herein with reference to illustrative embodiments and features, it will be appreciated that the embodiments and features described hereinabove are not intended to limit the invention, and that other variations, modifications and other embodiments will readily suggest themselves to those of ordinary skill in the art, based on the disclosure herein. The invention therefore is to be broadly construed, consistent with the claims hereafter set forth.

What is claimed is:

1. A circuitry for monitoring an electrochemical process in an electrochemical cell including working, reference and counter electrodes, arranged to carry out galvanostatic and potentiostatic modes of operation of said electrochemical cell, involving electrochemical plating in a galvanostatic mode of operation, and stripping, cyclic voltammetry, equilibration and nucleation in a potentiostatic mode of operation, said circuitry comprising a microcontroller programmably arranged in a feedback loop with said electrochemical cell, and circuit elements between said microcontroller and electrochemical cell for switching between galvanostatic and potentiostatic modes of operation of said electrochemical cell, wherein said circuitry comprises a CMOS analog switch including a first set of switch positions connectable to one another for said galvanostatic mode of operation, and a second set of switch positions connectable to one another for said potentiostatic mode of operation, a current control digital-to-analog converter arranged for linking to said working electrode and to said CMOS analog switch, and adapted to bring the circuitry to a predetermined current condition for said galvanostatic mode of operation, and a potential control digital-to-analog converter arranged for linking to said CMOS analog switch and to said reference electrode, and adapted to bring the circuitry to a predetermined potential condition for said potentiostatic mode of operation, and wherein said current control digital-to-analog converter and said potential control digital-to-analog converter are respectively adapted to provide rise time, to said predetermined current condition in said galvanostatic mode of operation, and to said predetermined potential condition in said potentiostatic mode of operation, of less than one millisecond, and with said CMOS analog switch arranged for linking with said counter electrode.

2. The circuitry of claim 1, which is devoid of analog switches other than said CMOS analog switch.

3. The circuitry of claim 1, wherein the microcontroller is programmably arranged to inject an offset voltage in said feedback loop corresponding to an operating potential range of said circuitry.

4. The circuitry of claim 3, operatively coupled with a unipolar power supply, wherein said operating potential range of said circuitry is within a potential range of said unipolar power supply.

5. The circuitry of claim 3, wherein the microcontroller is programmably arranged to modulate the offset voltage to control electrical potential across the electrochemical cell within a potential range accommodated by a unipolar power supply in both of said potentiostatic and galvanostatic modes of operation.

6. The circuitry of claim 3, which is devoid of analog switches other than said CMOS analog switch.

7. The circuitry of claim 1, which is devoid of mechanical switches.

8. The circuitry of claim 1, operatively coupled to said electrochemical cell, wherein said microcontroller is arranged for monitoring of a copper electrodeposition process.

9. The circuitry of claim 1, wherein said microcontroller is programmably arranged for carrying out a pulsed cyclic galvanostatic analysis procedure in said galvanostatic mode of operation.

10. The circuitry of claim 1, operatively coupled to a computational unit arranged to produce a monitoring output indicative of concentration of a species of interest in an electrochemical process conducted in said electrochemical cell, when the electrochemical process is monitored by said circuitry.

11. The circuitry of claim 1, wherein a portion of said circuitry for linking said CMOS analog switch to said counter electrode contains a first relay, and a second portion of said circuitry for linking the current control digital-to-analog converter with the working electrode contains a second relay, to provide open circuit capability so that the electrochemical cell can be rendered electrically inactive when fluids in the electrochemical cell are changed.

12. A circuitry for monitoring an electrochemical process in an electrochemical cell, said circuitry comprising a microcontroller programmably arranged in a feedback loop with said electrochemical cell, and circuit elements between said microcontroller and electrochemical cell for switching between galvanostatic and potentiostatic modes of operation of said electrochemical cell, said circuitry comprising:

a first analog-to-digital converter operatively linked to said electrochemical cell and arranged to input to said microcontroller a first digital signal correlative of a voltage in said electrochemical cell, in said galvanostatic mode of operation of said electrochemical cell;

a second analog-to-digital converter coupled with the electrochemical cell and arranged to input to said microcontroller a second digital signal correlative of current passing through said electrochemical cell, in said galvanostatic mode of operation of said electrochemical cell;

a first digital-to-analog convener linked to (i) said microcontroller for receiving a potential control digital signal from said microcontroller, and (ii) said electrochemical cell, for transmitting thereto a fixed voltage for measurement of electrochemical cell current in said potentiostatic mode of operation of said electrochemical cell;

a second digital-to-analog converter linked to said microcontroller for receiving an offset voltage digital signal from said microcontroller and responsively producing an analog signal for modulating the current for voltage measurement of the response of said electrochemical cell;

an operational amplifier having a first input thereof linked to said electrochemical cell, a second input thereof linked to said second digital-to-analog converter for receiving said analog signal for modulating potentiostatic measurement of response of said electrochemical cell, and an output linked to said second analog-to-digital converter for transmission of an output signal to said second analog-to-digital converter, wherein the operational amplifier is arranged to amplify current required to maintain said offset voltage in said potentiostatic mode of operation of said electrochemical cell; and a current measurement scaling unit coupled between said output and said first input of said operational amplifier, and arranged to set scaling of said output signal from the operational amplifier.

13. The circuitry of claim 12, wherein said current measuring scaling unit is arranged to set scaling of said output signal from the operational amplifier at a level enabling the circuitry to be powered by a unipolar power supply in both of said potentiostatic and galvanostatic modes of operation.

14. The circuitry of claim 12, further comprising a buffer linked between said electrochemical cell and said first analog-to-digital converter.

15. A method of monitoring an electrochemical process in an electrochemical cell, said method comprising subjecting the contents of the electrochemical cell to a potentiostatic mode and a galvanostatic mode of analysis by a microprocessor programmably arranged in a feedback loop with said electrochemical cell utilizing a monitoring circuitry comprising a microcontroller programmably arranged in a feedback loop with said electrochemical cell, and circuit elements between said microcontroller and electrochemical cell for switching between galvanostatic and potentiostatic modes of operation of said electrochemical cell, wherein said circuitry comprises a CMOS analog switch including a first set of switch positions connectable to one another for said galvanostatic mode of operation, and a second set of switch positions connectable to one another for said potentiostatic mode of operation, a current control digital-to-analog converter arranged for linking to said working electrode and to said CMOS analog switch, and adapted to bring the circuitry to a predetermined current condition for said galvanostatic mode of operation, and a potential control digital-to-analog converter arranged for linking to said CMOS analog switch and to said reference electrode, and adapted to bring the circuitry to a predetermined potential condition for said potentiostatic mode of operation, and wherein said current control digital-to-analog converter and said potential control digital-to-analog converter are respectively adapted to provide rise time, to said predetermined current condition in said galvanostatic mode of operation, and to said predetermined potential condition in said potentiostatic mode of operation, of less than one millisecond, and with said CMOS analog switch arranged for linking with said counter electrode.

16. A method of monitoring an electrochemical process in an electrochemical cell in accordance with claim 15, wherein said microcontroller-selectively applies galvanostatic or potentiostatic, or both, conditions on the electrochemical cell for measurement of response of the electrochemical cell to such conditions, and generates an offset potential to control potential across the electrochemical cell within a range of potential accommodated by a unipolar power supply.

17. The method of claim 16, wherein the said galvanostatic and potentiostatic conditions are applied by the microcontroller without analog switching steps.

18. The method of claim 16, wherein the said galvanostatic and potentiostatic conditions are applied by the microcontroller without mechanical switching steps.

19. The method of claim 16, further comprising use of a unipolar power supply as a power source for said microcontroller and electrochemical cell.

* * * * *